US012571786B2

(12) United States Patent
Jung et al.

(10) Patent No.: US 12,571,786 B2
(45) Date of Patent: Mar. 10, 2026

(54) METHOD OF MANUFACTURING METAL NANOPARTICLE-OXIDE SUPPORT COMPLEX STRUCTURE BASED GAS SENSOR

(71) Applicant: KOREA ADVANCED INSTITUTE OF SCIENCE AND TECHNOLOGY, Daejeon (KR)

(72) Inventors: WooChul Jung, Daejeon (KR); Il-Doo Kim, Daejeon (KR); Jun Kyu Kim, Daejeon (KR); Ji-Soo Jang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 447 days.

(21) Appl. No.: 17/411,202

(22) Filed: Aug. 25, 2021

(65) Prior Publication Data

US 2022/0170899 A1 Jun. 2, 2022

(30) Foreign Application Priority Data

Nov. 27, 2020 (KR) ........................ 10-2020-0162532

(51) Int. Cl.
| | |
|---|---|
| *G01N 33/00* | (2006.01) |
| *C01G 55/00* | (2006.01) |
| *G01N 33/497* | (2006.01) |

(52) U.S. Cl.
CPC ....... *G01N 33/0044* (2013.01); *C01G 55/002* (2013.01); *C01G 55/004* (2013.01); *G01N 33/497* (2013.01); *C01P 2002/34* (2013.01); *C01P 2004/04* (2013.01); *C01P 2004/64* (2013.01); *G01N 33/4975* (2024.05)

(58) Field of Classification Search
CPC .. C01G 55/002; C01G 55/004; C01G 23/002; G01N 33/0044; G01N 33/497; G01N 2033/4975; C01P 2002/34
See application file for complete search history.

(56) References Cited

U.S. PATENT DOCUMENTS

2011/0294038 A1* 12/2011 Kwon ................. H01M 4/8605
429/525

FOREIGN PATENT DOCUMENTS

| CN | 107561133 | | 1/2018 | |
|---|---|---|---|---|
| KR | 2019018851 | A * | 2/2019 | .............. B01J 23/40 |
| KR | 10-2019-0074378 | | 6/2019 | |
| KR | 20190074378 | A * | 6/2019 | |
| KR | 20190097752 | A * | 8/2019 | |

OTHER PUBLICATIONS

Osama et al, Structural and catalytic properties of ZnO and Al2O3 nanostructures loaded with metal nanoparticles, 2011, Journal of Nanoparticle Research, 13, 7075-7083 (Year: 2011).*

(Continued)

*Primary Examiner* — Elizabeth A Robinson
*Assistant Examiner* — Austin Q Le
(74) *Attorney, Agent, or Firm* — LEX IP MEISTER, PLLC

(57) ABSTRACT

Provided is a method of producing a metal nanoparticle-oxide support complex structure, in which metal nanoparticles uniform in size are evenly distributed on the surface of oxide supports. A gas sensor with improved gas sensing ability and durability may be provided by using the same.

9 Claims, 2 Drawing Sheets

(56)               References Cited

OTHER PUBLICATIONS

Li et al, Enhancing NH3 sensing performance of mixed potential type sensors by chemical exsolution of Ag nanoparticle on AgNbO3 sensing electrode, 2019, Sensors & Actuators B: Chemical, 298 (Year: 2019).*

Oun et al, Multifunctional nanocellulose/metal and metal oxide nanoparticle hybridnanomaterials, 2020, Critical Reviews in Food Science and Nutrition, vol. 6, issue 3, pp. 435-460 (Year: 2020).*

Calford Wai-Ting Chan et al., "Protamine-Induced Supramolecular Self-Assembly of Red-Emissive Alkynylplatinum(II) 2,6-Bis(benzimidazol-2'-yl)pyridine Complex for Selective Label-Free Sensing of Heparin and Real-Time Monitoring of Trypsin Activity", ACS Appl. Mater. Interfaces (Aug. 22, 2019).

Ji-Soo Jang et al., "Dopant-Driven Positive Reinforcement in Ex-Solution Process: New Strategy to Develop Highly Capable and Durable Catalytic Materials", Adv. Mater. 2020, 32, 2003983, Oct. 1, 2020.

Xu Li et al., "In situ exsolution of PdO nanoparticles from non-stoichiometric LaFePd0.05O3+δ electrode for impedancemetric NO2 sensor", Sensors & Actuators B: Chemical 298 (2019) 126827, Jul. 18, 2019.

* cited by examiner

[FIG. 1]
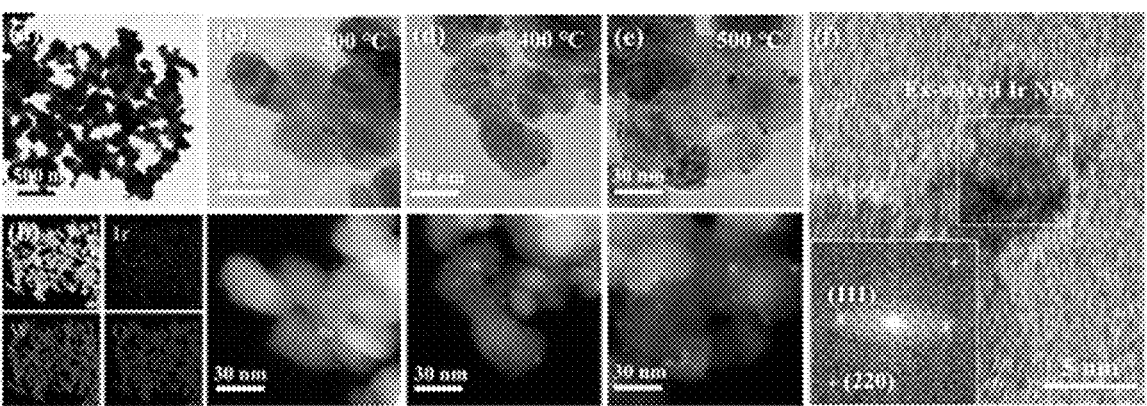
[FIG. 2]
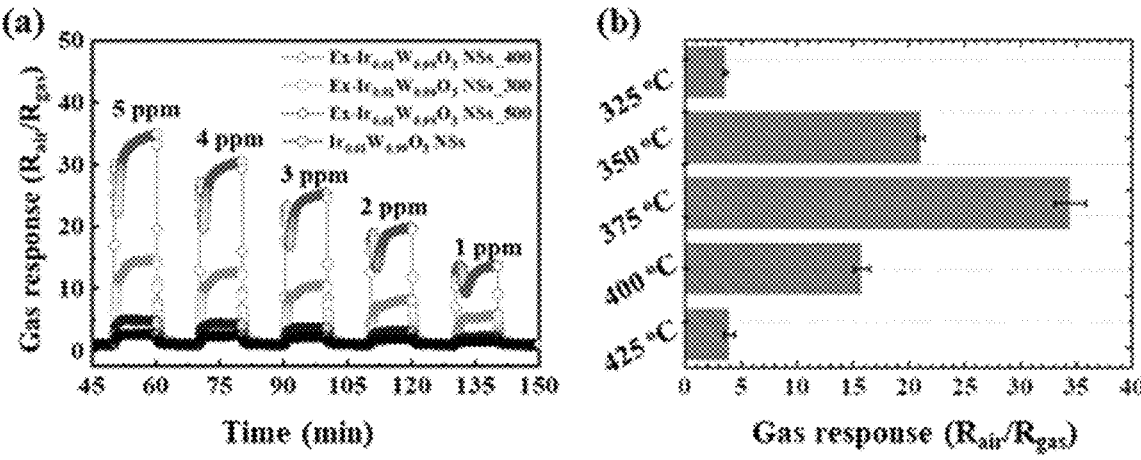

[FIG. 3]
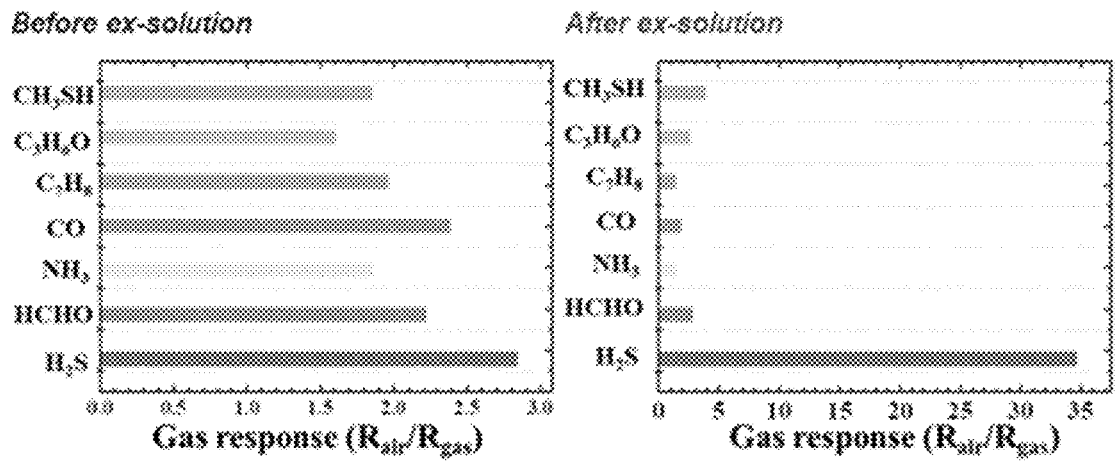
[FIG. 4]
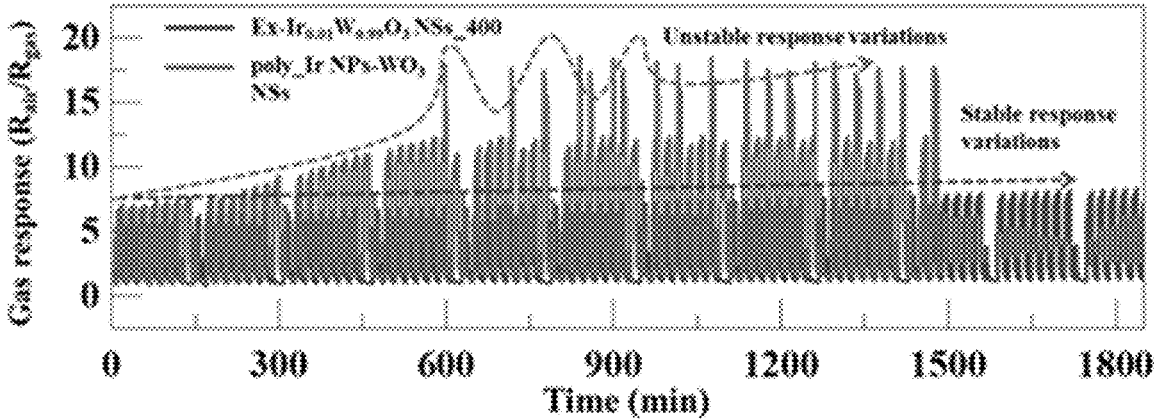

METHOD OF MANUFACTURING METAL NANOPARTICLE-OXIDE SUPPORT COMPLEX STRUCTURE BASED GAS SENSOR

TECHNICAL FIELD

The present invention relates to a method of manufacturing a complex structure-based gas sensor, in which metal nanoparticles uniform in size are evenly distributed on oxide supports.

BACKGROUND ART

A metal nanoparticle-oxide support type gas detection sensor manufactured by functionalizing a metal species with excellent catalytic activity in the form of nanoparticles on oxide supports has excellent gas sensitivity, selectivity, and high cost effectiveness, and thus is receiving global attention academically/industrially in the fields of exhaled breath sensors that detect a disease with a biomarker gas generated from exhaled breath according to a person's disease or environmental sensors that are used for air quality monitoring by detecting toxic gases such as formaldehyde, acetone, toluene, etc.

Until now, these gas sensor structures (or supported catalysts) have been mainly produced by physically mixing and depositing particles and oxides by physical mixing, physical vapor deposition, chemical vapor deposition, impregnation, etc., or by functionalizing nanoparticles on oxide supports using an external deposition process. The biggest problem of this prior art is that desorption and aggregation of metal nanoparticles occur due to a weak binding force between metal nanoparticles and oxide when the manufacturing process is actually performed and a sensing reaction is driven, and accordingly, the fluctuation range of the sensor sensitivity increases. This phenomenon eventually deteriorates reliability of the sensitivity and reproducibility of sensing materials, leading to deterioration of the gas sensor.

Accordingly, it is necessary to develop a new technology for producing a structure for a sensing material or a supported catalyst having excellent durability, even when metal nanoparticles having a uniform size are evenly dispersed on oxide supports.

DISCLOSURE

Technical Problem

There is provided a method of producing a metal nanoparticle-oxide support complex structure, in which durability, uniformity, and dispersibility of metal nanoparticles are improved.

Further, there is provided a gas sensor including the metal nanoparticle-oxide support complex structure.

Technical Solution

There is provided a method of producing a metal nanoparticle-oxide support complex structure, the method including a step (step 1) of mixing a precursor of the metal nanoparticle with a precursor of the oxide support; a step (step 2) of preparing a solid solution by calcining and sintering the mixture of the step 1; and a step (step 3) of forming the metal nanoparticles on the surface of the oxide supports by heat-treating the solid solution of the step 2 in a reducing atmosphere.

There is also provided a gas sensor including the metal nanoparticle-oxide support complex structure.

In the present invention, the terms "the first", "the second", and the like are used to describe a variety of components, and these terms are merely employed to differentiate one component from other components.

Further, the terms used in this description are just for explaining exemplary embodiments, and are not intended to restrict the present invention.

The singular expression may include the plural expression unless it is differently expressed contextually.

It must be understood that the term "include", "equip", or "have" in the present description is only used for designating the existence of characteristics taken effect, numbers, steps, components, or combinations thereof, and do not exclude the existence or the possibility of addition of one or more different characteristics, numbers, steps, components, or combinations thereof beforehand.

In the present specification, when a layer or an element is mentioned to be formed "on" or "above" layers or elements, it means that each layer or element is directly formed on the layers or elements, or other layers or elements may be formed between the layers, subjects, or substrates.

The present invention may be variously modified and have various forms, and specific exemplary embodiments will be illustrated and described in detail below. However, it is not intended to limit the present invention to the specific exemplary embodiments and it must be understood that the present invention includes every modifications, equivalents, or replacements included in the spirit and technical scope of the present invention.

As used herein, the term "complex structure" refers to a single structure, in which metal particles and oxide supports are physically and chemically bound.

Further, the term "metal nanoparticle-oxide support complex structure" refers to a structure, in which metal nanoparticles are formed on the surface of the supports made of oxide. In this regard, the shape of the oxide structure is not particularly limited, but the shape is preferably a plane shape such as a layer.

Hereinafter, the present invention will be descried in detail.

The present invention relates to a method of producing a metal nanoparticle-oxide support complex structure, the method including a step (step 1) of mixing a precursor of the metal nanoparticle with a precursor of the oxide support; a step (step 2) of preparing a solid solution by calcining and sintering the mixture of the step 1; and a step (step 3) of forming the metal nanoparticles on the surface of the oxide supports by heat-treating the solid solution of the step 2 in a reducing atmosphere.

(Step 1)

Step 1 is a step of mixing a precursor of the metal nanoparticle with a precursor of the oxide support. A method of mixing the precursor of the metal nanoparticle and the precursor of the oxide support is not particularly limited. However, the method may be, for example, a method of mixing an aqueous solution of the precursor of the metal nanoparticle with an aqueous solution of the precursor of the oxide support, followed by stirring.

Further, in the step 1, a template structure may be additionally mixed with the precursor of the metal nanoparticles and the precursor of the oxide support. As used herein, the template structure is a material that may be used to form a predetermined structure of a compound, and when the template structure is used, there is an advantage in that the structure of the metal nanoparticle-oxide support complex structure may be appropriately controlled. In particular, when additional mixing is performed in the step 1, it is easy to form the oxide support into a desired structure through step 2 and step 3 described below, and metal nanoparticles may be uniformly distributed on the oxide supports. Preferably, the template structure may be graphene oxide, nanocellulose, or a mixture thereof. In particular, when a mixture of graphene oxide and nanocellulose is used, the nanocellulose is bound to the surface of the graphene oxide, thereby improving the metal ion trapping property. In addition, other structure-forming materials may be additionally used for uniform mixing of the precursor mixture and formation of an appropriate structure thereof.

A method of mixing with the template structure is not particularly limited, but the method may be, for example, a method of mixing the aqueous precursor solution of the metal nanoparticles and the aqueous precursor solution of the oxide supports with an aqueous solution of the template structure. As described, the aqueous precursor solution of the metal nanoparticles and the aqueous precursor solution of the oxide supports, and the aqueous solution of the template structure were mixed with each other in an aqueous solution, and then centrifuged to obtain a product, which is then subjected to step 2 and step 3 to prepare a complex structure.

Meanwhile, the precursor of the metal nanoparticle may preferably include one or more selected from the group consisting of an iridium (Ir) salt, a palladium (Pd) salt, a ruthenium (Ru) salt, a rhodium (Rh) salt, a silver (Ag) salt, a gold (Au) salt, and a platinum (Pt) salt.

Further, the precursor of the oxide support may preferably include one or more selected from the group consisting of a tungsten (W) salt, a tin (Sn) salt, a zinc (Zn) salt, an iron (Fe) salt, and a titanium (Ti) salt.

Further, the oxide support may be a compound represented by the following Chemical Formula 1:

$$B_yO_z \qquad \text{[Chemical Formula 1]}$$

in Chemical Formula 1,
B is W, Sn, Zn, Fe, or Ti,
y is 1 to 3, and
z is 1 to 4.

Further, the precursor of the metal nanoparticle and the precursor of the oxide support may be mixed at a molar ratio of 5:95 to 1:99.

(Step 2)

In the present invention, step 2 is a step of preparing a solid solution by calcining and sintering the mixture of the precursor of the metal nanoparticle and the precursor of the oxide support, which is prepared in the step 1, and more specifically, is a step of preparing the solid solution by calcining and sintering the mixture of the precursor of the metal nanoparticle and the precursor of the oxide support which are uniformly mixed in the form of ions in an oxidizing atmosphere through step 1.

In the solid solution prepared through the step 2, the metal, support, and oxygen which are components may be uniformly dispersed. In addition, when the template structure is additionally mixed, the solid solution has a predetermined structure. For example, when a mixture of graphene oxide and nanocellulose is used as the template structure, the solid solution has a sheet-like structure having a porous structure. In addition, when the template structure is mixed together in step 1, the template structure may be removed through this step.

The step 2 may be performed by increasing the temperature from room temperature to 400° C. to 800° C. at a heating rate of 1° C./min to 10° C./min. More preferably, the step 2 may be performed at 500° C. to 600° C. When the temperature of the step 2 is lower than 400° C., the precursors are not thermally decomposed, which may generate a problem in the structure formation, and when the temperature is higher than 800° C., there may be a problem of the collapse of the structure.

(Step 3)

Step 3 is a step of forming the metal nanoparticles on the surface of the oxide supports by heat-treating the solid solution prepared in the step 2 in a reducing atmosphere.

More specifically, the step 3 is a step of growing metal nanoparticles from the oxide solid solution in real time using an "ex-solution" phenomenon. The present inventors have continued studies, and as a result, they have found that there is a difference in the reducing property between the metal and the oxide support constituting the solid solution, and reduction of the metal is easier than reduction of the oxide support, and thus when the solid solution is heat-treated in a reducing atmosphere, the metal is reduced on the surface of oxide support to be eluted (ex-solved) in the form of nanoparticles. They have also found that doping of the metal element accelerates a phase change of the support, and the phase change of the support accelerates the "ex-solution" phenomenon through a domino effect that promotes elution of the doped metal element into nanoparticles.

The size and dispersity of the metal nanoparticles formed in the step 3 may be controlled by conditions set during ex-solution, i.e., reducing heat treatment conditions. As described, the reducing heat treatment conditions that influence the formation of metal nanoparticles may include the type, concentration, heat treatment temperature and time of a reducing gas.

Specifically, according to one embodiment of the present invention, in the step 3, any one or more of a $H_2$/Ar mixed gas, a $H_2$/$H_2O$ mixed gas, a $CO$/$CO_2$ mixed gas, and a $H_2$/$N_2$ mixed gas may be used. In addition, a volume ratio of the $H_2$/Ar mixed gas, $H_2$/$H_2O$ mixed gas, $CO$/$CO_2$ mixed gas, or $H_2$/$N_2$ mixed gas may be preferably 1/99 to 99/1. When the volume ratio of the mixed gas is less than 1/99, the reduction of metal particles may not occur well, and thus nanoparticles may not be formed. When the volume ratio is more than 99/1, the uniformity or dispersibility of the metal nanoparticles may deteriorate due to excessive reduction.

Further, the step 3 may be performed at 200° C. to 600° C. Preferably, the step 3 may be performed at 250° C. to 550° C. When the heat treatment temperature of the step 3 is lower than 200° C., the reduction of metal particles may not occur well, and thus nanoparticles may not be formed. When the heat treatment temperature is higher than 600° C., the dispersibility of the metal nanoparticles may deteriorate due to excessive reduction, and the structure of the complex structure may collapse.

The above-described metal nanoparticle-oxide support complex structure prepared according to the present invention may be a compound represented by the following Chemical Formula 2:

$$A_xB_yO_z \qquad \text{[Chemical Formula 2]}$$

in Chemical Formula 2,
A is the metal nanoparticle,
B is W, Sn, Zn, Fe, or Ti, x is 0.005 to 0.1, y is 0.9 to 2.995, and z is 1 to 4.

In Chemical Formula 2, x and y represent a ratio of the metal and oxide support elements in the metal nanoparticle-oxide support complex structure, respectively, x may be 0.005 to 0.1, y may be 0.9 to 2.995, and preferably, x may be 0.005 to 0.05, and y may be 0.95 to 2.995.

As described, since the "ex-solution" is a spontaneous phase separation phenomenon, there is an advantage in that synthesis and dispersion of the nanoparticles simultaneously occur without additional processing by exposing them to a reducing atmosphere. In addition, unlike nanoparticles randomly dispersed in a metal/oxide structure prepared by traditional metal particle deposition techniques, the nanoparticles are eluted from the uniformly mixed solid solution, and thus the nanoparticles are uniformly dispersed on the oxide supports and have high thermal and chemical stability. Therefore, the metal nanoparticle-oxide support complex structure produced by using the "ex-solution" phenomenon may have nanoparticle durability, uniformity, and dispersibility at levels which are difficult to achieve by the existing nanoparticle functionalization process.

Meanwhile, the present invention provides a gas sensor including the metal nanoparticle-oxide support complex structure prepared by the above-described preparation method. The type of gas detectable by the gas sensor of the present invention is not particularly limited, but the gas may be, for example, $CH_3SH$, $C_3H_6O$, $C_7H_8$, CO, $NH_3$, HCHO, $H_2S$, or a mixture thereof. In particular, the gas sensor shows excellent detection performance for $H_2S$.

As described above, the metal nanoparticle-oxide support complex structure produced by using the "ex-solution" phenomenon has excellent gas sensitivity and selectivity, and excellent durability without deterioration in the performance even after long-term use.

In addition, the metal nanoparticle-oxide support complex structure produced according to the present invention also has high applicability as a heterogeneous catalyst.

Effect of the Invention

The present invention may provide a metal nanoparticle-oxide support complex structure having improved durability, in which metal nanoparticles uniform in size are evenly distributed on the surface of oxide supports.

The present invention may also provide a high-performance gas sensor including the metal nanoparticle-oxide support complex structure, of which long-term use is possible.

BRIEF DESCRIPTION OF DRAWINGS

FIG. 1 shows observation results according to Experimental Example 1 of the present invention;

FIG. 2 shows observation results according to Experimental Example 2 of the present invention;

FIG. 3 shows observation results according to Experimental Example 3 of the present invention; and FIG. 4 shows observation results according to Experimental Example 4 of the present invention.

DETAILED DESCRIPTION OF THE EMBODIMENTS

Hereinafter, the actions and effects of the present invention will be described in more detail with reference to the specific exemplary embodiments. However, these exemplary embodiments are only for illustrating the present invention, and the scope of the present invention is not limited thereto.

EXAMPLE

Example 1

A graphene oxide (GO) solution (1.2 mL, 5 mg/mL) and an aqueous nanocellulose (NC) solution (10 mL) were mixed to prepare a graphene oxide-nanocellulose solution (GO-NC). Thereafter, ammonium metatungstate hydrate ($(NH_4)_6H_2W_{12}O_{40}$, 0.123 g) and iridium chloride ($IrCl_3 \cdot xH_2O$, 5 mg) were dissolved in deionized water (24 mL) to prepare a tungsten/iridium solution (W/Ir sol). The prepared tungsten/iridium solution was added to the GO-NC solution, and stirred at 300 rpm for 3 hours to prepare a W/Ir_GO-NC solution.

The prepared W/Ir_GO-NC solution was centrifuged to obtain a pellet, which was then dried at 50° C. for 6 hours. Then, the W/Ir_GO-NC solution in a gel state was heated to 600° C. at 5° C./min, and then calcined for 1 hour to 3 hours to prepare 1 at % Ir-doped $WO_3$ nanosheets ($Ir_{0.01}W_{0.99}O_3$ NSs). For ex-solution treatment, the prepared $Ir_{0.01}W_{0.99}O_3$ NSs were reduced under conditions of $H_2/Ar$ (4/96, (v/v)), 300° C. for 1 hour to prepare a final Ir—$WO_3$ complex structure.

Example 2

An Ir—$WO_3$ complex structure was prepared in the same manner as in Example 1, except that the prepared $Ir_{0.01}W_{0.99}O_3$ NSs were reduced at 400° C.

Example 3

An Ir—$WO_3$ complex structure was prepared in the same manner as in Example 1, except that the prepared $Ir_{0.01}W_{0.99}O_3$ NSs were reduced at 500° C.

Comparative Example 1

An Ir—$WO_3$ complex structure was prepared in the same manner as in Example 1, except that the prepared $Ir_{0.01}W_{0.99}O_3$ NSs were not reduced.

Comparative Example 2

$WO_3$ NSs were prepared in the same manner as in Example 1, except that the iridium chloride precursor was not used, and reduction using the $H_2/Ar$ gas was not performed. Then, iridium nanoparticles were impregnated in $WO_3$ NSs at 1 at % by impregnation to prepare an Ir—$WO_3$ complex structure (poly_Ir NPs-$WO_3$).

Experimental Example

Experimental Example 1

During the preparation of Examples 1 to 3 and Comparative Example 1, the surface of each complex structure was observed by TEM, and the results are shown in FIG. 1.

Experimental Example 2

Each of the complex structures of Examples 1 to 3 and Comparative Example 1 was dispersed in ethanol and then coated onto an alumina sensor substrate (2.5 mm×2.5 mm) with a gold electrode (width=2.5 μm, gap size=150 μm) to manufacture each gas sensor.

Then, after stabilization in dry air (30% RH; relative humidity), the gas sensor was exposed to $H_2S$ at 1 ppm to 5 ppm while the sensor was turned on and off at 10 min intervals, and its sensing characteristics were measured. The results are shown in FIG. 2A.

In addition, the sensing characteristics of the complex structure of Example 2 were measured according to the temperature of $H_2S$, and the results are shown in FIG. 2B.

Experimental Example 3

Each gas sensor was manufactured using the complex structure of Example 2 or Comparative Example 1 in the same manner as in the method of Experimental Example 2.

Then, after stabilization in dry air (30% RH), the gas sensor was exposed to $CH_3SH$, $C_3H_6O$, $C_7H_8$, CO, $NH_3$, HCHO, or $H_2S$ while the sensor was turned on and off at 10 min intervals, respectively, and sensing characteristics thereof were measured. The results are shown in FIG. 3.

Experimental Example 4

Each gas sensor was manufactured using the complex structure of Example 2 or Comparative Example 2 in the same manner as in the method of Experimental Example 2.

Then, after stabilization in dry air (30% RH), the gas sensor was exposed to 1 ppm of $H_2S$ while the sensor was turned on and off at 10 min intervals, and sensing characteristics were measured for a long period of time. The results are shown in FIG. 4.

The invention claimed is:

1. A method of producing a metal nanoparticle-oxide support complex structure, the method comprising:
   a step (step 1) of mixing a precursor of the metal nanoparticle with a precursor of the oxide support to form a first mixture and additionally mixing a mixture of graphene oxide and nanocellulose with the first mixture of the precursor of the metal nanoparticle and the precursor of the oxide support to form a second mixture, wherein the second mixture consists of the precursor of the metal nanoparticle, the precursor of the oxide support, graphene oxide, and nanocellulose;
   a step (step 2) of preparing a solid solution by calcining and sintering the second mixture of the step 1; and a step (step 3) of forming the metal nanoparticles on the surface of the oxide supports by heat-treating the solid solution of the step 2 in a reducing atmosphere,
   wherein the graphene oxide and the nanocellulose are removed through the step 2, and
   wherein the precursor of the metal nanoparticle is an iridium (Ir) salt, and the precursor of the oxide support is a tungsten (W) salt.

2. The method of claim 1, wherein the oxide support is a compound represented by the following Chemical Formula 1:

$$B_yO_z \qquad \text{[Chemical Formula 1]}$$

in Chemical Formula 1,
   B is W,
   y is 1 to 3, and
   z is 1 to 4.

3. The method of claim 1, wherein the precursor of the metal nanoparticle and the precursor of the oxide support are mixed at a molar ratio of 5:95 to 1:99.

4. The method of claim 1, wherein the step 2 is performed by raising the temperature from room temperature to 400° C. to 800° C. at a heating rate of 1° C./min to 10° C./min.

5. The method of claim 1, wherein the step 3 is performed by using any one or more of a $H_2$/Ar mixed gas, a $H_2$/$H_2O$ mixed gas, a CO/$CO_2$ mixed gas, and a $H_2$/$N_2$ mixed gas.

6. The method of claim 5, wherein a volume ratio of the $H_2$/Ar mixed gas, the $H_2$/$H_2O$ mixed gas, the CO/$CO_2$ mixed gas, or the $H_2$/$N_2$ mixed gas is 1/99 to 99/1.

7. The method of claim 1, wherein the step 3 is performed at 200° C. to 600° C.

8. The method of claim 1, wherein the metal nanoparticle-oxide support complex structure is a compound represented by the following Chemical Formula 2:

$$A_xB_yO_z \qquad \text{[Chemical Formula 2]}$$

in Chemical Formula 2,
   A is the metal nanoparticle,
   B is W,
   x is 0.005 to 0.1,
   y is 0.9 to 2.995, and
   z is 1 to 4.

9. A gas sensor comprising the metal nanoparticle-oxide support complex structure of claim 1.

* * * * *